(12) United States Patent
Isozaki et al.

(10) Patent No.: US 6,587,192 B2
(45) Date of Patent: Jul. 1, 2003

(54) SURFACE INSPECTING APPARATUS AND METHOD

(75) Inventors: Hisashi Isozaki, Tokyo (JP); Yutaka Shida, Tokyo (JP)

(73) Assignee: Kabushiki Kaisha Topcon, Tokyo (JP)

( * ) Notice: Subject to any disclaimer, the term of this patent is extended or adjusted under 35 U.S.C. 154(b) by 41 days.

(21) Appl. No.: 09/785,530

(22) Filed: Feb. 20, 2001

(65) Prior Publication Data

US 2002/0005945 A1 Jan. 17, 2002

(30) Foreign Application Priority Data

Feb. 25, 2000 (JP) ........................................ 2000-049300

(51) Int. Cl.$^7$ .............................................. G01N 21/00
(52) U.S. Cl. ................. 356/237.2; 356/237.3; 356/237.4
(58) Field of Search ................... 356/237.1, 237.2, 356/237.3, 237.4, 237.5; 250/559.4, 559.41, 559.42, 559.45

(56) References Cited

U.S. PATENT DOCUMENTS 5,903,342 A * 5/1999 Yatsugake et al. ....... 356/237.4
5,912,732 A * 6/1999 Sekine ..................... 356/237.5
6,104,481 A * 8/2000 Sekine et al. ............ 356/237.5
6,384,910 B2 * 5/2002 Vaez-Iravani et al. ... 356/237.2

* cited by examiner

Primary Examiner—Georgia Epps
Assistant Examiner—M. Hasan
(74) Attorney, Agent, or Firm—Foley & Lardner

(57) ABSTRACT

A surface inspection apparatus includes a light source section for emitting first and second luminous fluxes; a first irradiation optical system which irradiates the first luminous flux on an inspected object at a first irradiation angle; a second irradiation optical system which irradiates the second luminous flux on an inspected object at a second irradiation angle; a light receiving optical system for receiving scattered light of the first and second luminous fluxes; first and second light receiving sections for converting the scattered light of the first and second luminous fluxes into first and second light receiving signals, respectively; a displacement section for relatively displacing an inspected object and an irradiation luminous flux of the irradiation optical system; and a discrimination section for discriminating the kind of inspection object based on the strength of the scattered light and the scattered range of the first and second light receiving signals.

24 Claims, 11 Drawing Sheets

SURFACE INSPECTING APPARATUS AND METHOD

FIELD OF THE INVENTION

The present invention relates to a surface inspection apparatus and a surface inspection method for inspection in objects, for example, such as foreign matter, scratches, or COP (Crystal Defect) on the surface of a wafer and other inspected objects.

PRIOR ART

In the prior art, foreign matters on the surface of an inspected object have been measured by placing a luminous flux incident in the form of high incidence or low incidence on the surface of an inspected object.

However, with the trend of higher sensitivity of the inspection apparatus and fineness of steps, in the conventional surface inspection apparatus and the surface inspection method, for example, in a Bare-Si, it has been impossible to correctly separate the grow-in defect (fine crystal defect) on the surface or extremely thin foreign matter of residual matter caused by the surface polishing from the conventional foreign matter to measure them.

There has been proposed an example in which data of a measuring apparatus on the high incident side and data of a measuring apparatus on the low incident side are superposed, and from comparison therebetween, the inspection object is discriminated from the foreign matter.

It has been impossible to separate the conventional foreign matter or thin crystal defect from extremely fine foreign matter which is a residual matter caused by the surface polishing step to detect them.

With the trend of higher sensitivity of the inspection and fineness of steps, particularly in a Bare-Si, it has been desired to correctly separate the grow-in defect (fine crystal defect) on the surface or extremely thin foreign matter of residual matter caused by the surface polishing from the conventional foreign matter to measure them.

Further, it has been desired apparatus and method for separating micro scratches or slurries caused by CMP (Chemical Mechanical Process) that cannot be avoided in the fineness art to detect them with high sensitivity.

SUMMARY OF THE INVENTION

It is an object of the present invention to provide a surface inspection method and a surface inspection apparatus in which at least two different luminous fluxes are incident at different angles, scattered light of not less than two luminous fluxes incident at respective angles are separated by wavelength or polarized light, and the inspection object is discriminated on the basis of the scattering strength of the respective scattered light and the range of the scattered light.

It is a further object of the present invention to provide a surface inspection apparatus and a surface inspection method in which two different luminous fluxes are incident at different angles, scattered light of luminous fluxes incident at respective angles are separated by wavelength or polarized light, and the inspection object is discriminated on the basis of the scattering strength of the respective scattered light and the range of the scattered light and according to the kind of inspected objects.

The present invention relates to an improvement in a surface inspection apparatus and a surface inspection method for inspection objects, for example, such as foreign matter, scratches, or COP (crystal defect) on the surface of a wafer and other inspected objects.

According to one mode of the present invention, the surface inspection apparatus comprises a light source section for emitting a first luminous flux having a first characteristic and a second luminous flux having a second characteristic; a first irradiation optical system in which the first luminous flux is irradiated on the surface of an inspected object at a first irradiation angle; a second irradiation optical system in which the second luminous flux is irradiated on the surface of an inspected object at a second irradiation angle; a light receiving optical system for receiving the scattered light of the first luminous flux irradiated by the first irradiation optical system and generated from the inspection object on the surface of an inspected object and the scattered light of the second luminous flux irradiated by the second irradiation optical system and generated from the inspection object on the surface of an inspected object; a first light receiving section for converting the scattered light of the first luminous flux received by the light receiving optical system into a first light receiving signal; a second light receiving section for converting the scattered light of the second luminous flux received by the light receiving optical system into a second light receiving signal; a displacement section for relatively displacing an inspected object and an irradiation luminous flux of the irradiation optical system; and a discrimination section for discriminating the kind of the inspection object on an inspected object on the basis of the strength of scattered light of the first and second light receiving signals and the scattered range of the scattered light of the first and second light receiving signals.

Preferably, the first characteristic of the first luminous flux and the second characteristic of the second luminous flux emitted from the light source section are a wavelength of luminous flux or a polarized light component. The first irradiation angle of the first irradiation optical system is set to be smaller than the second irradiation angle of the second irradiation optical system.

Preferably, the discrimination section carries out the process of scattered light quantity ratio for obtaining the strength ratio of the scattered light of the first and second light receiving signals, and the process of scattered range detection for obtaining the scattered range of scattered light according to whether or not the first and second light receiving signals are at a level above a predetermined level. Further, the discrimination section carries out the discrimination processes as described below every position of the surface of an inspected object:

(A) When judgment is made that the scattered light generated from the inspection object is present in only one of either the first light receiving signal or the second light receiving signal, the first discrimination process for discriminating that the kind of the inspection object is a first inspection object is carried out.

(B) When judgment is made that the scattered light generated from the inspection object is present in both the first light receiving signal and the second light receiving signal, the ratio between the strength of scattered light of the first light receiving signal and the strength of scattered light of the second light receiving signal is obtained, and if the ratio is at a level above a predetermined level, the second discrimination process for discriminating that the kind of the inspection object is a second inspection object is carried out.

(C) When judgment is made that the scattered light generated from the inspection object is present in both the first light receiving signal and the second light receiving signal, the ratio between the strength of scattered light of the first light receiving signal and the strength of scattered light of the second light receiving signal is obtained, and the ratio is at a level above a predetermined level, and further, a first function due to the strength of scattered light and the scattered range of scattered light of the first light receiving signal and a second function due to the strength of scattered light and the scattered range of scattered light of the second light receiving signal are obtained, and when the ratio therebetween is at a value above a predetermined value, the discrimination process for discriminating that the kind of the inspection object is a third inspection object is carried out.

(D) When judgment is made that scattered light generated from the inspection object not falling under the process is present in the first light receiving signal or the second light receiving signal, the discrimination process for discriminating that the kind of the inspection object is normal foreign matter is carried out.

Preferably, the kind of the inspection object discriminated by the discrimination section is decided according to the kind of the inspected object.

For example, where the inspected object is a bare semiconductor wafer (Bare-Si), the discrimination section discriminates that the first inspection object is COP (crystal defect) by the first discrimination process; that the second inspection object is COP (crystal defect) by the second discrimination process; and that the third inspection object is extremely thin foreign matter by the third discrimination process.

Further, preferably, where the inspected object is a semiconductor wafer after CMP (chemical mechanical process) process of a wafer with a membrane, the discrimination section discriminates that the first foreign matter is COP (crystal defect) by the first discrimination process; that the second foreign matter is micro scratch by the second discrimination process; and that the third foreign matter is micro scratch by the third discrimination process.

DESCRIPTION OF THE PREFERRED EMBODIMENTS

Figure 1:
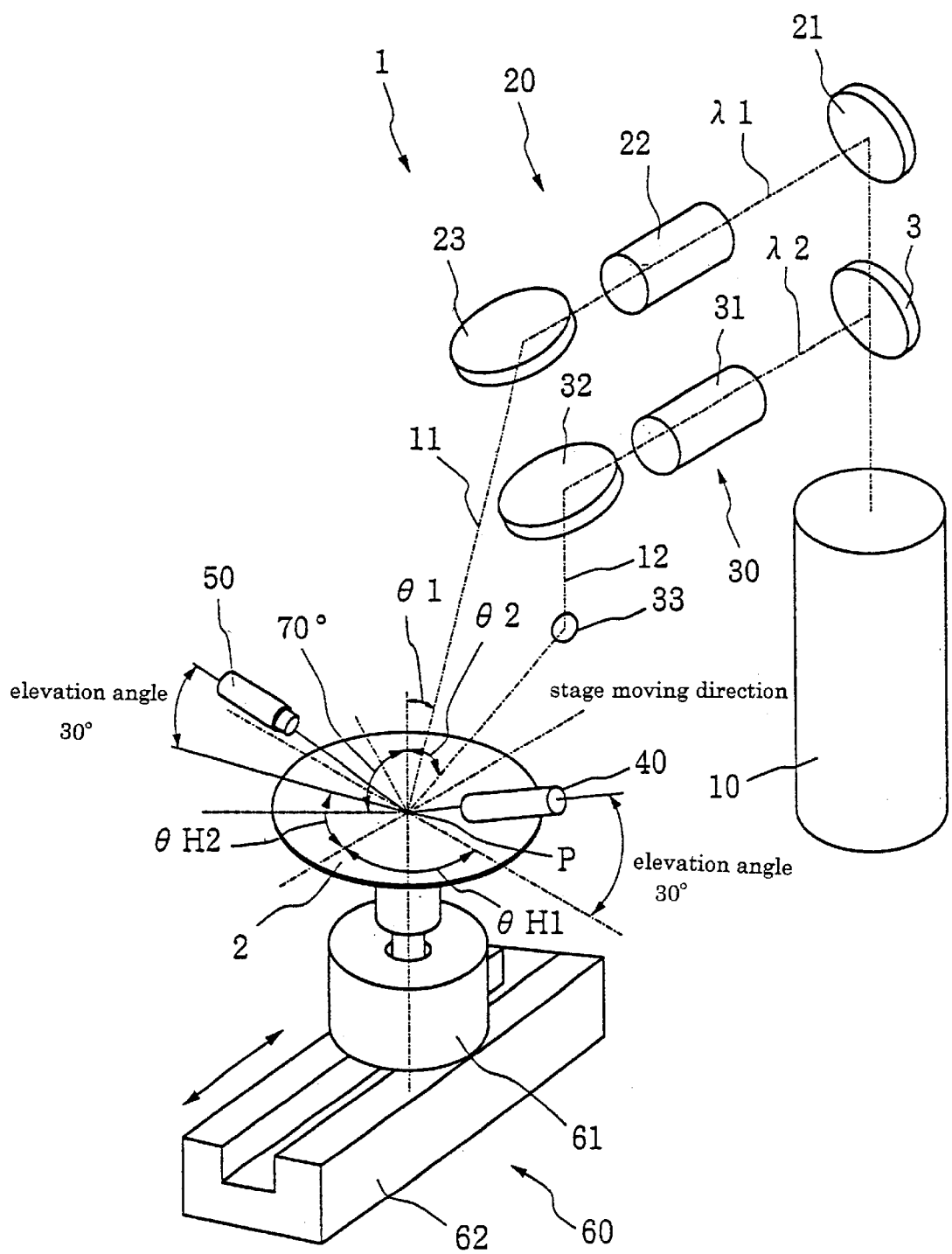
FIG. 1 is a schematic arrangement view of main optical elements of a surface inspection apparatus according to one embodiment of the present invention.

FIG. 1 is a schematic arrangement view of main optical elements of a surface inspection apparatus according to preferred one embodiment of the present invention.

A surface inspection apparatus 1 comprises a light source section 10 such as a laser tube for emitting at least a luminous flux 11 of a first wavelength $\lambda 1$ and a luminous flux 12 of a second wavelength $\lambda 2$, a first irradiation optical system 20 for irradiating the luminous flux 11 of a first wavelength $\lambda 1$ from the light source section 10 on a semiconductor wafer 2 as an inspected object at a first irradiation angle $\theta 1$, a second irradiation optical system 30 for irradiating the luminous flux 12 of a second wavelength $\lambda 2$ from the light source section 10 on an inspection point P on the surface of the semiconductor wafer 2 at a second irradiation angle $\theta 2$ similarly to the first irradiation optical system 20, a first light receiving optical system 40 for receiving scattered light from an inspection point P on the surface of the semiconductor wafer 2 caused by the luminous fluxes 11, 12 irradiated by the first irradiation optical system 20 and the second irradiation optical system 30 in a first light receiving direction, a second light receiving optical system 50 for receiving scattered light from an inspection point P on the surface of the semiconductor wafer 2 caused by the luminous fluxes 11, 12 irradiated by the first irradiation optical system 20 or the second irradiation optical system 30 in a second light receiving direction different from the first light receiving direction, and a displacement section 60 for allowing the semiconductor wafer 2 as an inspected object to enable straight and rotational movement relatively with respect to the luminous flux 11 of the first irradiation optical system 20. An angle of elevation of the first light receiving optical system 40 is 30° and an angle of elevation of the second light receiving optical system 50 is 30°.

Figure 12:
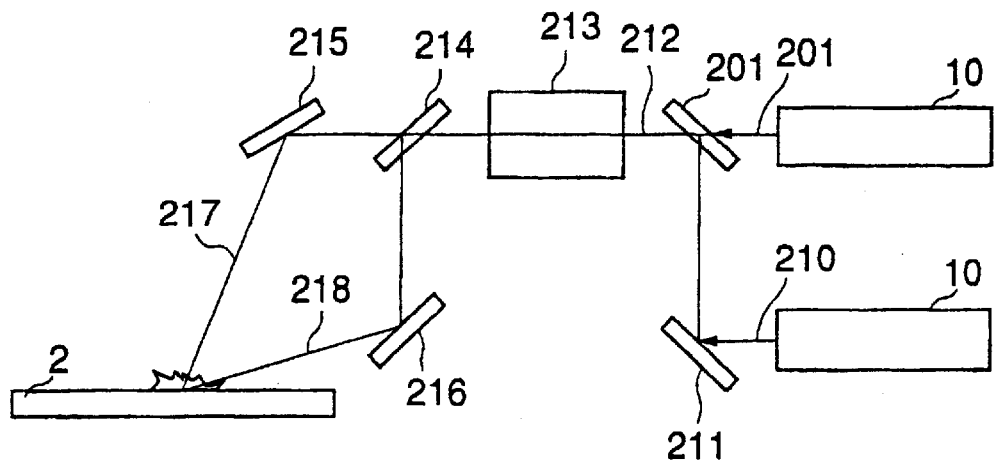
FIG. 12 is a system block diagram showing the situation that two luminous fluxes having different wavelengths are incident at different incident angles in the surface inspection apparatus according to a preferred embodiment of the present invention.

The light source section 10 will be explained. As the light source section 10 for emitting at least the luminous flux 11 of a first wavelength, the second luminous flux 12 of a second wavelength different therefrom, various kinds of sources for emitting luminous fluxes of a plurality of wavelengths can be used. For example, employed are one that luminous fluxes of a plurality of wavelengths are emitted by a single light source, for example, such as a laser of multi-line, and the other that luminous fluxes of a plurality of light sources emitting fluxes of different wavelengths are combined by a half mirror or the like to form a single beam.

Where when a laser of multi-line is employed, luminous fluxes of unnecessary wavelength emit, the flux is caused to pass through a band pass filter passing through the first wavelength and the second wavelength to thereby enable extraction of only the luminous flux of necessary wavelength.

Where a plurality of light sources emitting luminous fluxes of different wavelengths is used, a plurality of luminous fluxes are combined by a half mirror or the like to form a single beam. One example is shown in FIG. 12. A beam (luminous flux) 210 is emitted from two light sources 10, and reflected by a mirror 211, after which they are combined by a half mirror 201 halfway to make a combined beam 212. In the combined beam 212, luminous fluxes 217 and 218 of two kinds of wavelengths are irradiated on an inspected object 2 at different incident angles through a lens unit 213 and a series of mirrors 214 to 216. For example, a helium cadmium laser is used to select a wavelength of 441.6 nm and a wavelength of 325 nm.

In an example of FIG. 1, if an argon ion laser is used as the light source section 10, a wavelength of 488 nm and a wavelength of 514.5 nm can be selected. A luminous flux emitted from the light source section 10 causes the luminous flux 11 of a first wavelength $\lambda 1$ to pass through, and the luminous flux 11 of a first wavelength and the luminous flux 12 of a second wavelength to be separated by a dichroic mirror 3 to reflect the luminous flux 12 of a second wavelength $\lambda 2$. The luminous flux 11 of a first wavelength is changed in direction by a first mirror 21, and is irradiated on an irradiation point P on the surface of an inspected object 2 at a first irradiation angle $\theta 1$ through a group of first irradiation lenses 22 and a second mirror 23. The luminous flux 12 of a second wavelength is reflected by a dichroic mirror 3, and is irradiated on an irradiation point P on the surface of an inspected object 2 at a second irradiation angle $\theta 2$ through a group of second irradiation lenses 31, a third mirror 32 and a fourth mirror 33.

Where an inspection object, that is, such as foreign matter is present on the irradiation point P on the surface of the inspected object 2, when the irradiation luminous flux is irradiated thereon, scattered light occurs in accordance with a predetermined directivity. The first irradiation angle $\theta 1$ and the second irradiation angle $\theta 2$ are set with a normal direction of the inspected object 2 as a reference. In the embodiment of FIG. 1, as the first irradiation angle $\theta 1$, a predetermined angle is selected from the range of 0 to 40 degree as an incident angle. As the second irradiation angle $\theta 2$, a predetermined angle is selected from the range of 50 to 85 degree. The horizontal direction may be either the same or different.

In the embodiment of FIG. 1, there is established a relationship of the first irradiation angle $\theta 1$<the second irradiation angle $\theta 2$. The magnitude of the first wavelength $\lambda 1$ and the second wavelength $\lambda 2$ can be optionally selected. Since there is the tendency that the larger the incident angle, the detection sensitivity is enhanced, and the shorter the using wavelength $\lambda$, the detection sensitivity is enhanced, if the second wavelength $\lambda 2$ is shorter than the first wavelength $\lambda 1$ (the first wavelength $\lambda 1$>the second wavelength $\lambda 2$), it can be set in a direction that the detection sensitivity due to the first irradiation angle $\theta 1$ is equal to the detection sensitivity due to the second irradiation angle $\lambda 2$.

Next, the first light receiving optical system 40 (side scattered light) and the second light receiving optical system 50 (forward scattered light) will be explained.

The first light receiving optical system 40 and the second light receiving optical system 50 for receiving the aforementioned scattered light are provided. The first light receiving optical system 40 receives, from a first light receiving direction, the scattered light from the inspection point P on the surface of the semiconductor wafer 2 caused by the luminous fluxes 11, 12 irradiated by the first irradiation optical system 20 and the second irradiation optical system 30. The second light receiving optical system 50 receives, from a second light receiving direction different from the first light receiving direction, the scattered light from the inspection point P on the surface of the semiconductor wafer 2 caused by the luminous fluxes 11, 12 irradiated by the first irradiation optical system 20 or the second irradiation optical system 30.

A first light receiving horizontal angle $\theta H1$ (for example, 90°) in a first light receiving direction and a second light receiving horizontal angle $\theta H2$ (for example, 50°) in a second light receiving direction are measured, as a reference, a reflecting direction when the irradiation luminous fluxes 11, 12 caused by the first irradiation optical system 20 or the second irradiation optical system 30 is mirror-reflected by the inspected object 2. In the embodiment of FIG. 1, there is a relationship of the first light receiving horizontal angle $\theta H1$>the second light receiving horizontal angle $\theta H2$.

The light receiving elevation angle in the first and second light receiving direction is set, for example, to 30°.

Figure 2:
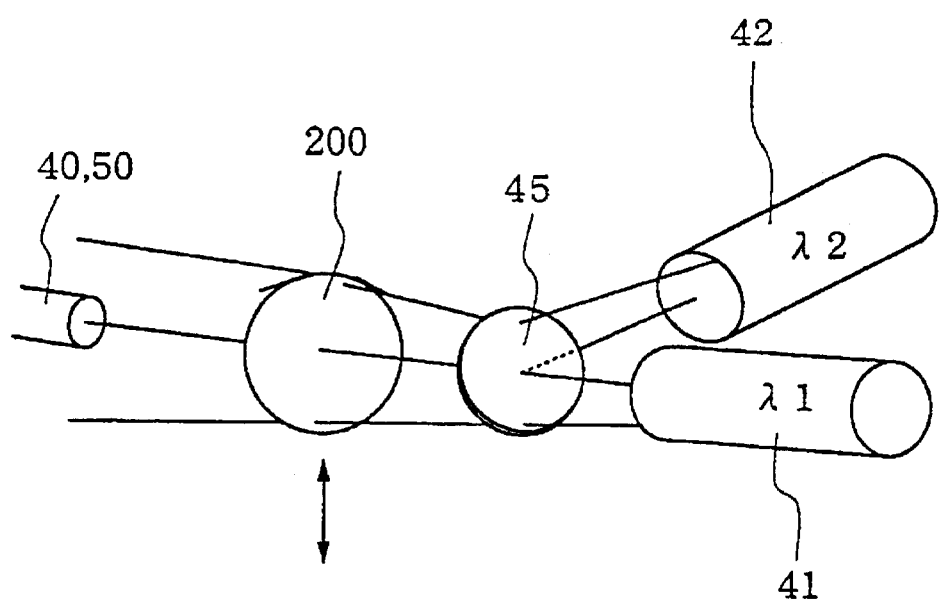
FIG. 2 is a detailed view of a light receiving optical system of the surface inspection apparatus according to one embodiment of the present invention.

As shown in FIG. 2, the luminous flux received by the first light receiving optical system 40 is separated by a second dichroic mirror 45 into the luminous flux of a first wavelength $\lambda 1$ and the luminous flux of a second wavelength $\lambda 2$ via a ND filter 200 arranged movably in a direction of arrow (vertical direction in FIG. 2) for being inserted in the light receiving path or being moved away therefrom. The first light receiving section 41 receives the scattered light of a first wavelength $\lambda 1$ received by the first light receiving optical system 40 to convert it into a first light receiving signal. The second light receiving section 42 receives the scattered light of a second wavelength $\lambda 2$ received by the first light receiving optical system 40 to convert it into a second light receiving signal.

Also in the second light receiving optical system 50, the luminous flux is separated by a dichroic mirror 45 into the luminous flux of a first wavelength $\lambda 1$ and the luminous flux of a second wavelength $\lambda 2$ via a ND filter 200 arranged movably in a direction of arrow (vertical direction in FIG. 2) by the optical system similar to that shown in FIG. 2. The third light receiving section 43 receives the scattered light of a first wavelength $\lambda 1$ received by the second light receiving optical system 50 to convert it into a third light receiving signal. The fourth light receiving section 44 receives the scattered light of a second wavelength $\lambda 2$ received by the second light receiving optical system 50 to convert it into a fourth light receiving signal.

The aforementioned first to fourth light receiving sections 41 to 44 are desired to be constituted by a light receiving element of high sensitivity such as a photomultiplier.

The displacement section 60 will now be described. The displacement section 60 comprises a rotation displacement section 61 for rotating and displacing an inspected object 2, and a straight-line displacement section 62 for straight-line displacing an inspected object 2. The straight-line displacement is merely moved at the fixed rate of the width of luminous flux with respect to displacement of one rotation of the rotation displacement section 61 to spirally scan the inspected object 2 throughout by irradiation light of the first and second irradiation optical systems 20, 30.

The present invention is not limited to the scanning method as described above, but the irradiation luminous flux may be subjected to straight-line scanning by a polygon mirror or the like in place of the rotation displacement.

In the embodiment of FIG. 1, the rotation displacement section 61 comprises a rotation motor for rotating a rotation table. The straight-line displacement section 62 comprises a slide movement section for moving the rotation motor linearly. The slide movement section causes, by movement thereof, an irradiation position of the irradiation luminous fluxes 11, 12 of the irradiation optical systems 20, 30 to be displaced so as to pass through the center of the inspected object 2 to cross in a diametrical direction.

Figure 3:
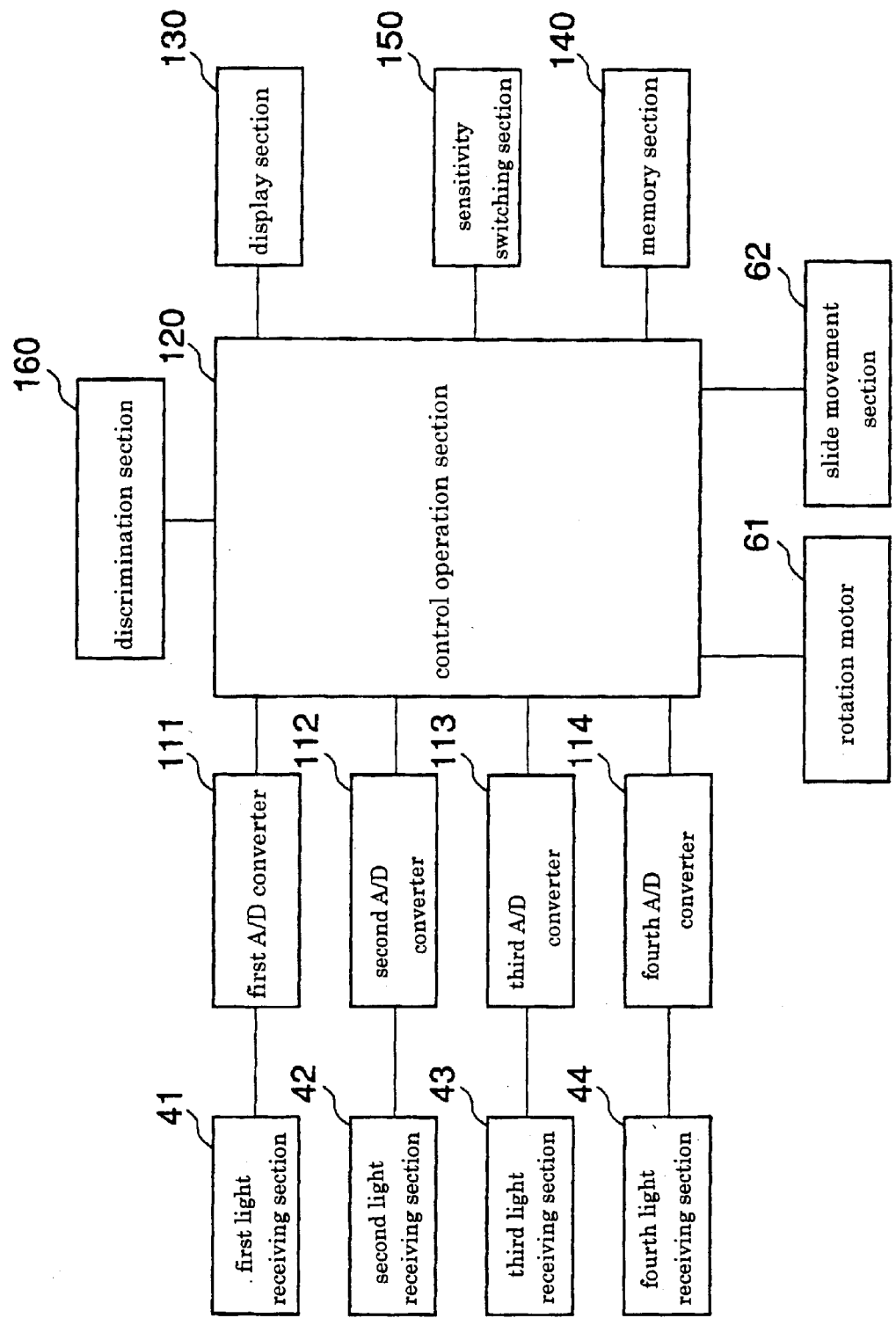
FIG. 3 is a block diagram of the surface inspection apparatus according to one embodiment of the present invention.

FIG. 3 is a block diagram of the surface inspection apparatus according to the present invention.

The first to fourth light receiving signals of the first to fourth light receiving sections 41, 42, 43, 44 are respectively converted into digital signals by the first to fourth A/D converters 111, 112, 113, 114 and thereafter are sent to a control operation section 120 for carrying out the function of the signal processing section to receive a predetermined signal processing. The control operation section 120 carries out selecting light receiving signals and predetermined signal processing described later to display the inspection result on a display section 130 as necessary, or to store it in a memory section 140 or to read the stored content.

Further, the control operation section 120 controls a discrimination section 160. The discrimination section 160 discriminates the kind of an inspection object on an inspected object described later.

Further, the control operation section 120 further controls the rotational motor of the rotation displacement section 61 and the slide movement section of the straight-line displacement section 62, or controls a sensitivity switching section 150 of the first to fourth light receiving sections 41, 42, 43, 44 according to the kind of the inspected object 2.

The sensitivity switching section 150 moves the ND filter 200 in a direction of arrow in FIG. 2 to insert the ND filter 200 into the light receiving window of the first to fourth light receiving sections 41, 42, 43, 44 to lower the sensitivity or to separate the ND filter 200 from the light receiving window to raise the sensitivity, thereby carrying out the switching of sensitivity.

When the first to fourth light receiving sections 41, 42, 43, 44 are formed from a photomultiplier, the sensitivity can be switched by regulation of voltage applied thereto.

The sensitivity switching of the light receiving section will be described.

When inspection is started, first, the kind of the inspected object 2 is discriminate. For example, discrimination is made whether it is one which is less surface scattering (for example, a bare wafer, with a $SiO_2$ membrane), or one which is many in the surface scattering (for example, a wafer with a metal membrane). When the inspected object 2 is one which is less in the surface scattering, setting is made that the sensitivity of the first to fourth light receiving sections 41 to 44 is suitable for the inspected object less in the surface scattering. That is, in case of the inspected object less in the surface scattering, the sensitivity of the first light receiving section 41 and the third light receiving section 43 is switched to the high sensitivity, and the sensitivity of the second light receiving section 42 and the fourth light receiving section 44 is switched to the low sensitivity for inspection.

When judgment is made that the kind of the inspected object 2 is one which is many in the surface scattering (for example, a wafer with a metal membrane), setting is made that the sensitivity of the first to fourth light receiving sections 41 to 44 is suitable for the inspected object many in the surface scattering. That is, in case of the inspected object many in the surface scattering, the sensitivity of the first light receiving section 41 and the third light receiving section 43 is switched to the low sensitivity, and the sensitivity of the second light receiving section 42 and the fourth light receiving section 44 is switched to the high sensitivity for inspection.

Next, selection of the light receiving signals by the control operation section 120 will be described.

Where the inspected object 2 is one which is less in the surface scattering (for example, a bare wafer, with a $SiO_2$ membrane), setting is made that the sensitivity of the first to fourth light receiving sections 41 to 44 is suitable for the inspected object less in the surface scattering. That is, in case of the inspected object less in the surface scattering, the sensitivity of the first light receiving section 41 and the third light receiving section 43 is switched to the high sensitivity, and the sensitivity of the second light receiving section 42 and the fourth light receiving section 44 is switched to the low sensitivity. In this state, inspection is carried out.

At this time, the scattered light of the first wavelength $\lambda 1$ caused by the luminous flux irradiated at a high angle is received by the first light receiving section 41 set to the high sensitivity and the second light receiving section 42 set to the low sensitivity to form the first light receiving signal and the second light receiving signal, respectively.

The scattered light of the second wavelength $\lambda 2$ caused by the luminous flux irradiated at a low angle is received by the third light receiving section 43 set to the high sensitivity and the fourth light receiving section 44 set to the low sensitivity to form the third light receiving signal and the fourth light receiving signal, respectively.

The light receiving signal for which the signal process for extracting the inspection object is carried out is decided according to the strength of the scattered light from the inspection object. The first light receiving signal or the second light receiving signal is selected for the object of the signal process as the signal of the scattered light having the first wavelength $\lambda 1$. Thereby, the scattering characteristics in case of the high angle irradiation is obtained.

On the other hand, with respect to the scattering characteristics in case of the low angle irradiation, the third light receiving signal or the fourth light receiving signal is selected for the object of the signal process as the signal of the scattered light having the second wavelength $\lambda 2$.

The selected light receiving signal is applied with the predetermined signal process by the control operation section 120. The control operation section 120 extracts the inspection object by the signal process to obtain the inspection object data.

The inspection object data comprises four elements, i.e., a start coordinate, a peak coordinate, an end coordinate and a peak level value.

Figure 4:
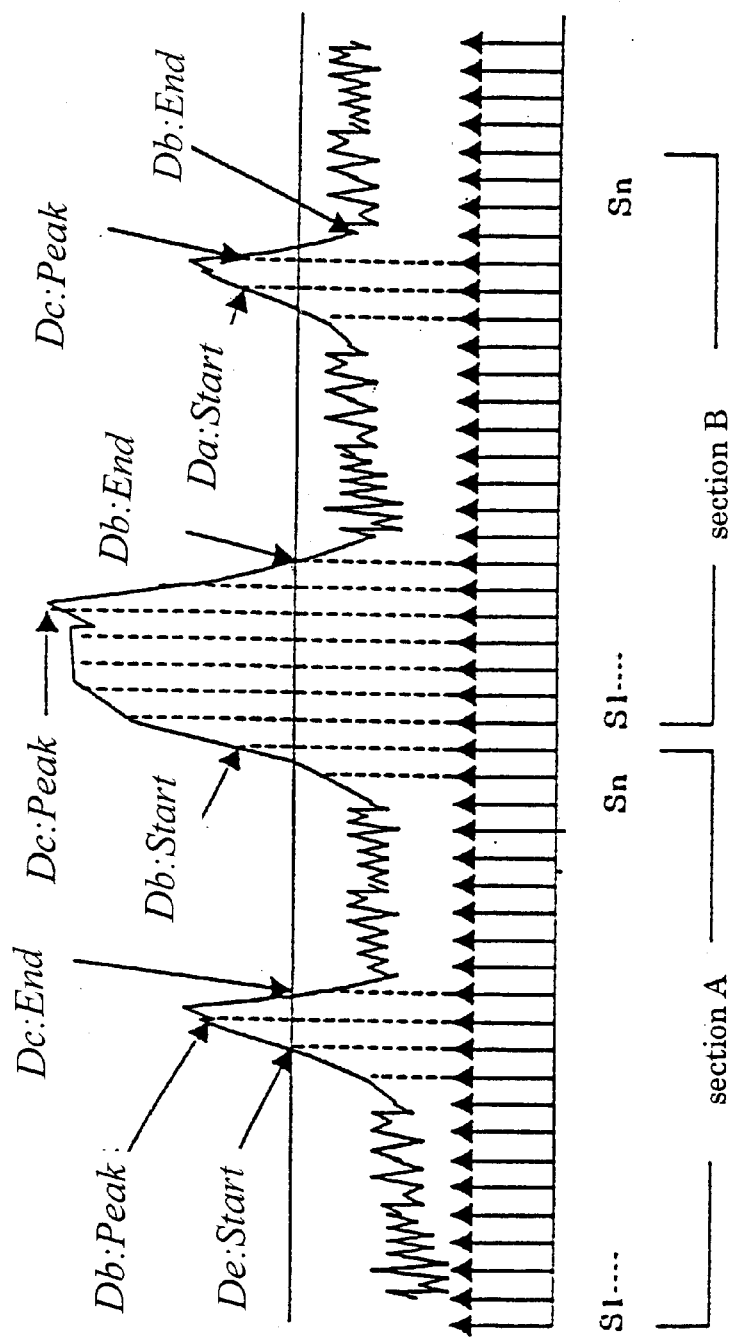
FIG. 4 is a view showing the construction of inspection object data in a light receiving signal in the surface inspection apparatus according to one embodiment of the present invention.
Figure 5:
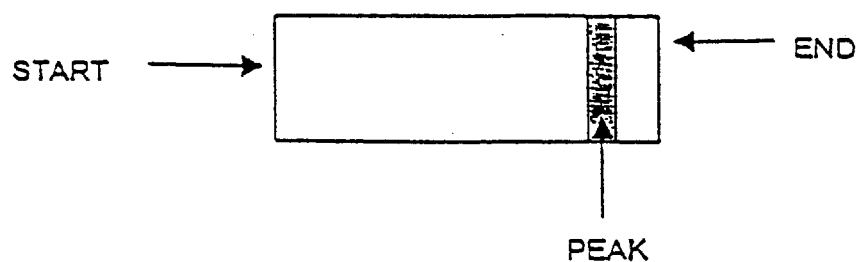
FIG. 5 is a schematic view of inspection object data in the surface inspection apparatus according to one embodiment of the present invention.

FIG. 4 is a view showing the construction of the inspection object data in the light receiving signal. FIG. 5 is a schematic view of the inspection object data.

When the scattered signal of the inspection object exceeds the threshold signal (shown by the solid line horizontally in FIG. 4) when the detection light is scanned in a predetermined direction, that is stored as the start coordinate (Start), and when the inspection object scattered signal is lowered than the threshold signal, that is stored as the end coordinate (End), and that the inspection object scattered signal is greatest between the start coordinate and the end coordinate is stored as the peak level value (Peak). The inspection object on the surface of the inspected object is specified on the basis of the inspection object data comprising a start coordinate (Start), a peak level value (Peak), and an end coordinate (End).

In FIG. 4, since as inspection objects, Da, Db and Dc are specified, the number of inspection objects is three. In this case, data between sections A and B has nothing to do with the number of inspection objects, and the number of inspection objects is counted as three.

Figure 6:
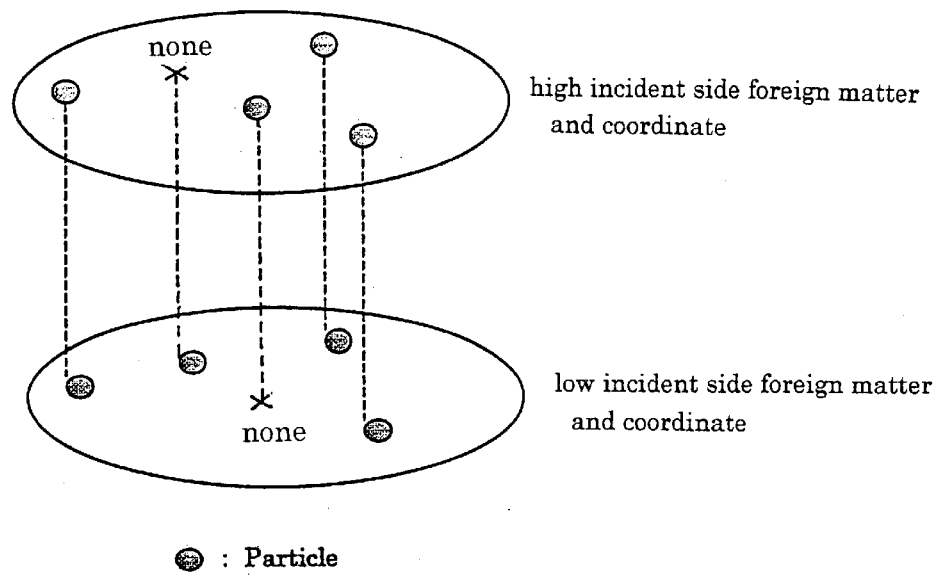
FIG. 6 is a view showing the alignment process of coordinates in the surface inspection apparatus according to one embodiment of the present invention.

FIG. 6 is a view showing the alignment process of coordinates described later.

The discrimination section 160 carries out the coordinate alignment using the several coordinates of inspection object data stored as described above, to adjust the coordinates on the high incident side to that on the low incident side.

Figure 7:
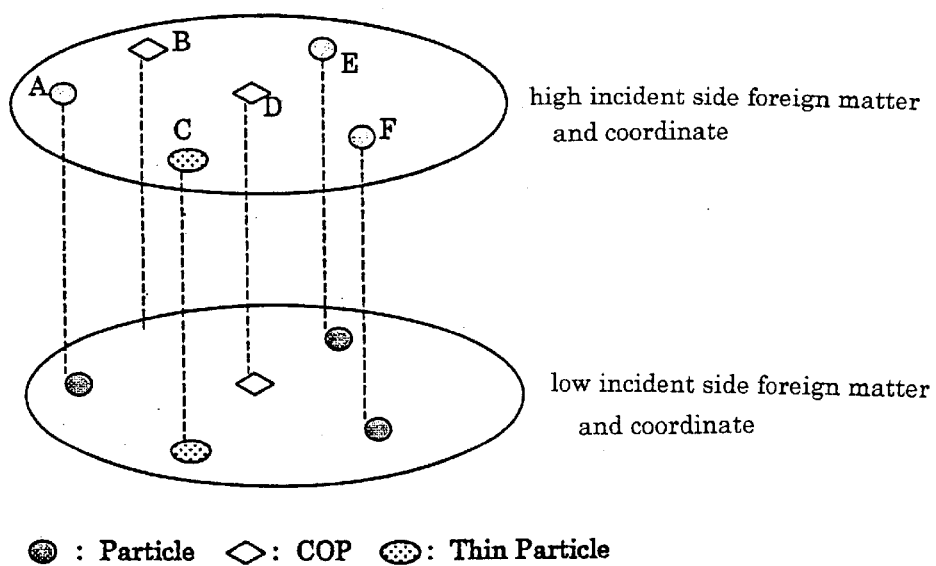
FIG. 7 is a view showing the inspection process in a bare wafer in the surface inspection apparatus according to one embodiment of the present invention.

FIG. 7 is a view showing the inspection process in a bare wafer.

After carrying out the coordinate alignment, the discrimination section 160 carries out a predetermined discrimination process described later to discriminate the kind of inspection objects. As a result, for example, the detection result as shown in FIG. 7 is obtained.

Figure 8:
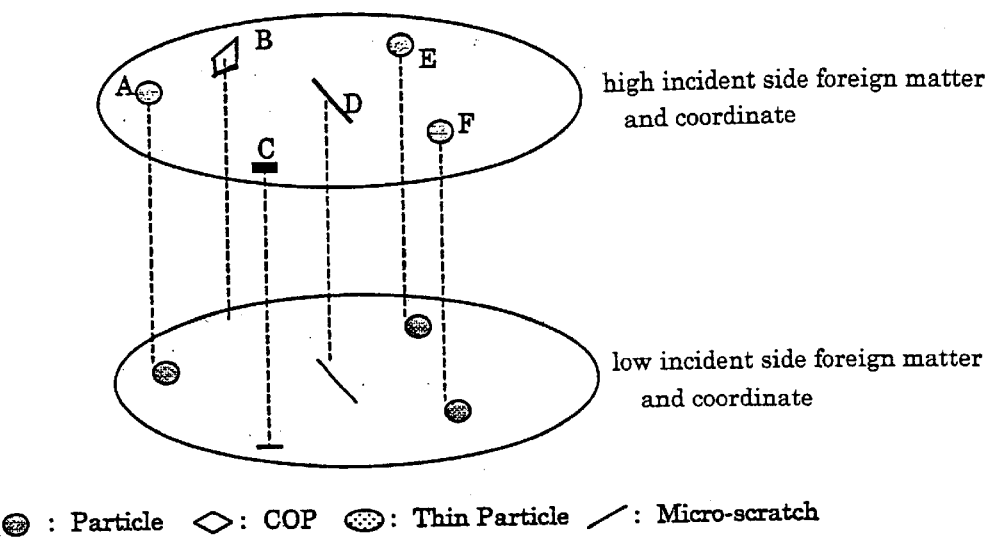
FIG. 8 is a view showing the inspection process in a waver with a membrane after CMP (chemical mechanical process) process in the surface inspection apparatus according to a preferred embodiment of the present invention.

FIG. 8 is a view showing the inspection process in a wafer with a membrane after CMP (chemical mechanical process) process.

After carrying out the coordinate alignment, the discrimination section 160 carries out a predetermined discrimination process described later to discriminate the kind of inspection objects. As a result, for example, the detection result as shown in FIG. 8 is obtained.

Next, the procedure for inspection will be described.

Figure 9:
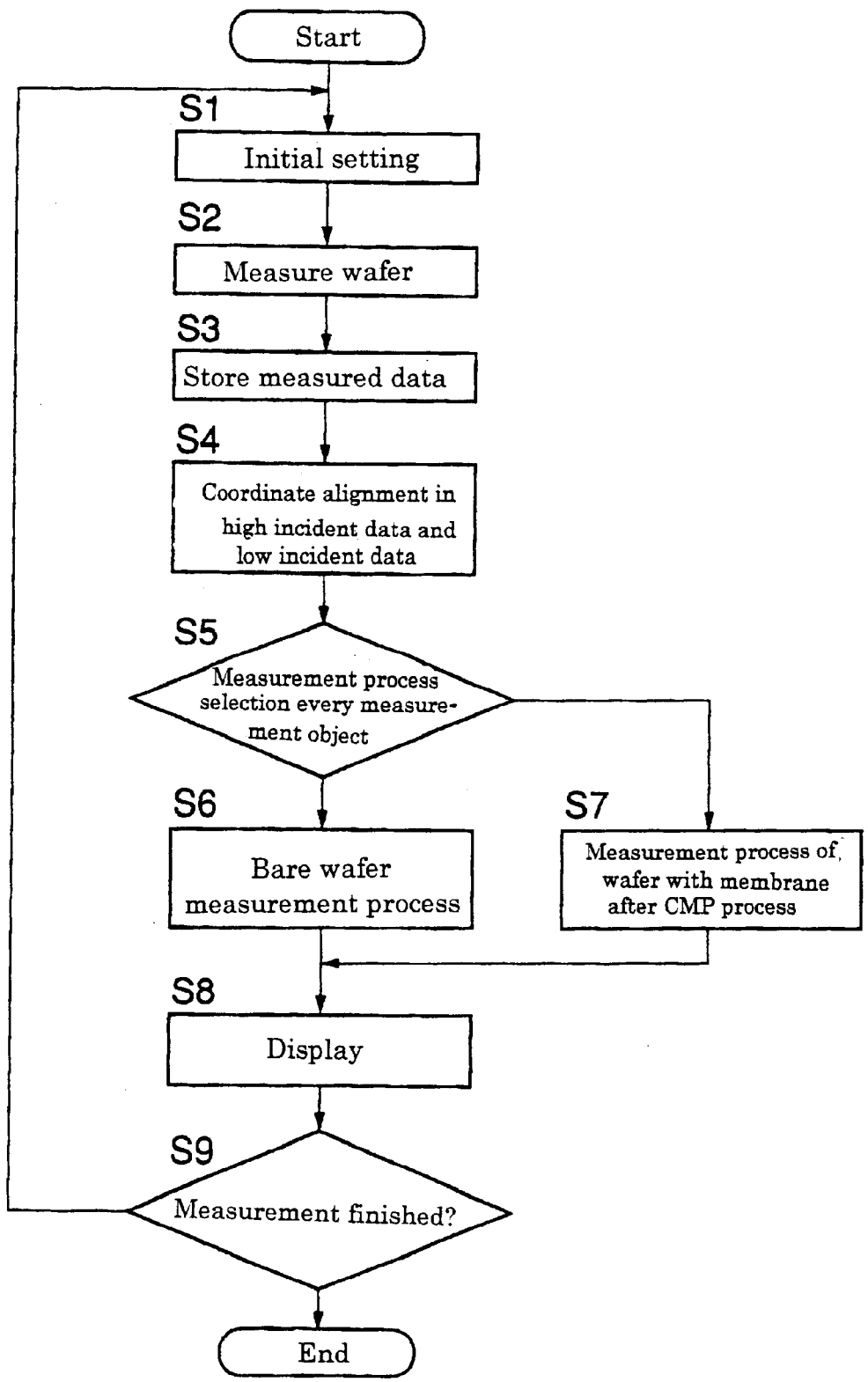
FIG. 9 is a view showing a flow chart showing the schematic inspection procedure in the surface inspection apparatus according to a preferred embodiment of the present invention.

FIG. 9 is a flow chart showing the rough procedure for inspection.

First, in Step S1, initial setting is carried out. In the initial setting, the kind of the inspected object 2 is discriminated so as to have setting that the sensitivity of the first to fourth light receiving sections 41 to 44 is suited to the inspected object discriminated.

In Step S2, in the state that both the luminous flux 11 of the first wavelength λ1 and the luminous flux 12 of the second wavelength λ2 are irradiated from the first irradiation optical system 20 and the second irradiation optical system 30, the displacement section 60 carries out rotational displacement and straight-line displacement to cause the wafer to effect rotation and straight-line movement to execute helical scanning. Next, the procedure proceeds to Step S3.

In Step S3, the control operation section 120 selects the light receiving signal as described above to store the light receiving signal in the memory section 140 as measured data. Next, the procedure proceeds to Step S4.

In Step S4, the discrimination section 160 carries out the extraction of inspection object data. The discrimination section 160 extracts a portion (inspection object data) exceeding the predetermined slice level in the high incident data of the measured data stored in the memory section 140 and the low incident data. The high incident data termed therein is measured data obtained by the luminous flux incident from a high position. The low incident data is measured data obtained by the luminous flux incident from a low position.

Further, the discrimination section 160 obtains the scattered range of the scattered light and the strength of the scattered light on the high incident side from the inspection object in the high incident data using the predetermined conditions (for example, there is a superposed portion as coordinates). Further, the discrimination section 160 obtains the scattered range of the scattered light and the strength of the scattered light on the low incident side from the inspection object in the low incident data using the predetermined conditions (for example, there is a superposed portion as coordinates). Then, the discrimination section 160 carries out the coordinate alignment to cause the inspection object data to correspond to the high incident side and the low incident side. Next, the procedure proceeds to Step S5.

In Step S5, the discrimination section 160 selects the kind of measuring process every measuring object. If the measuring object is a bare wafer, the procedure proceeds to Step S6 to discriminate the kind of the inspection object on the bare wafer. The discrimination results are combined in the control operation section 120, and the procedure proceeds to Step S8.

In Step S8, the discrimination result of the kind of the inspection object is displayed on the display section 130, and the procedure proceeds to Step S9.

In Step S9, judgment is made if the measuring is finished. If not, new measurement is carried out. If terminated, the procedure will finish.

In Step 5, where the measured object is a wafer with a membrane after the CMP process, the procedure proceeds to Step S7, and discrimination is made of the kind of the inspection object on the surface of the wafer with a membrane after the CMP process. The discrimination results are combined in the control operation section 120, and the procedure proceeds to Step S8.

In Step S8, the discrimination result of the kind of the inspection objects is displayed on the display section 130, and the procedure proceeds to Step S9.

In Step S9, judgment is made if the measuring is finished. If not, new measurement is carried out. If terminated, the procedure will finish.

In the following, the bare wafer measuring process in Step S6 in FIG. 9 will be described in detail.

Figure 10:
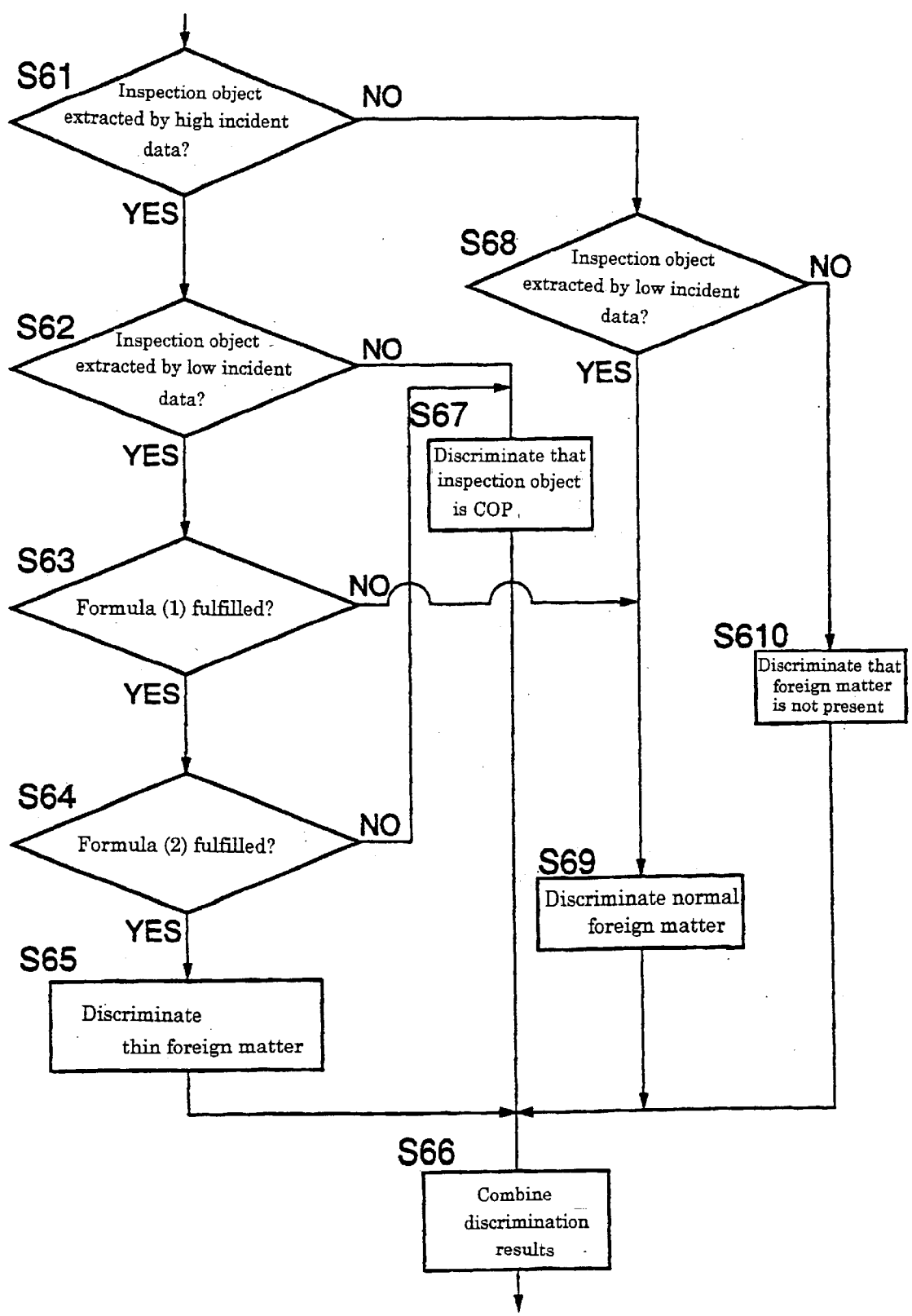
FIG. 10 is a view showing one example of a detailed flow chart of the measurement process of a bare wafer in the surface inspection apparatus according to a preferred embodiment of the present invention.

FIG. 10 shows one example of a detailed flow chart of the measuring process of a bare wafer.

The discrimination section 160 carries out discrimination of the kind of the inspection objects every coordinate on the surface of the inspected object on the basis of the result of the extraction process of the inspection object data carried out in Step S4 of the flow chart in FIG. 9. The method for the discrimination process of the kind of the inspection objects is as shown in the flow chart in FIG. 10.

First, in Step S61, judgment is made if whether or not the inspection object is extracted in the high incident data. If the inspection object is extracted in the high incident data, the procedure proceeds to Step S62.

In Step S62, judgment is made if whether or not the inspection object is extracted in the low incident data. If the inspection object is extracted in the low incident data, the procedure proceeds to Step S63.

In Step S63, judgment is made if the following formula (1) is fulfilled. high incident scattered level/low incident scattered level>1.5 . . . (1)

Here, the scattered level is the numerical value indicative of the strength of the scattered light. The formula (1) is a formula to judge if the ratio between the strengths of the scattered light on the high incident side and the low incident side is above a predetermined level.

If the formula (1) is fulfilled, the procedure proceeds to Step S64.

In Step S64, judgment is made if the following formula (2) is fulfilled.

F (high incident scan time, high incident scattered light quantity)/F (low incident scan time, low incident scattered light quantity)>2 . . . (2)

Here, F is a function with the scan time and the scattered light quantity as a variable. The scan time is a variable indicative of the scattered range of the scattered light. The scattered light quantity is a variable indicative of the strength of the scattered light. The formula (2) is a formula to judge if the ratio between the functions due to the strength of the scattered light and the scattered range of the scattered light on the high incident side and the low incident side is above a predetermined value.

If the formula (2) is fulfilled, the procedure proceeds to Step S65.

In Step S65, judgment is made that the kind of the inspection object is an extremely thin foreign matter, and the procedure proceeds to Step S66.

In Step S66, the discrimination result of the kind of the inspection object is combined with the discrimination result of the kind of the other inspection object on the surface of the bare wafer, and the procedure proceeds to Step S8 (FIG. 9), and the discrimination result of the kind of the inspection object is displayed on the display section 130.

In Step S64, where the formula (2) is not fulfilled, the procedure proceeds to Step S67. In Step S67, discrimination is made that the kind of the inspection object is COP (crystal defect), and the procedure proceeds to Step S66, and the discrimination results are combined.

In Step S63, if the formula (1) is not fulfilled, the procedure proceeds to Step S69.

In Step S69, judgment is made that the kind of the inspection object is normal foreign matter, and the procedure proceeds to Step S66, and the discrimination results are combined.

In Step S62, if the inspection object is not extracted in the low incident data, the procedure proceeds to Step S67. In Step S67, discrimination is made that the kind of the inspection object is COP (crystal defect), and the procedure proceeds to Step S66, and the discrimination results are combined.

In Step S61, if the inspection object is not extracted in the high incident data, the procedure proceeds to Step S68.

In Step S68, judgment is made if the inspection object is extracted in the low incident data. If the inspection object is extracted in the low incident data, the procedure proceeds to Step S69 to judge that the kind of the inspection object is normal foreign matter. Next, the procedure proceeds to Step S66 to combine the discrimination results.

In Step S68, if the inspection object is not extracted in the low incident data, the procedure proceeds to Step S610.

In Step S610, discrimination is made that the inspection object is not present (foreign matter or COP is not present), and the procedure proceeds to Step S66. In Step S66, the discrimination results are combined.

Table 1 shows one example of a discrimination table of the kind of the inspection object of a bare wafer according to the flow chart of FIG. 10.

In the formula (2) of Table 1, F is a function with the scan time and the scattered light quantity as a variable.

The detection result is obtained, for example, as shown in FIG. 7, by the measuring process described above.

In FIG. 7, the inspection objects A, E, F are detected as foreign matter (Particle). The inspection object B is detected as COP (crystal defect). The inspection object D is detected as COP (crystal defect). The inspection object C is detected as a thin foreign matter (Thin Particle).

The measuring process of a wafer with a membrane after CMP process in Step S7 in FIG., 9 will be described in detail thereinafter.

Figure 11:
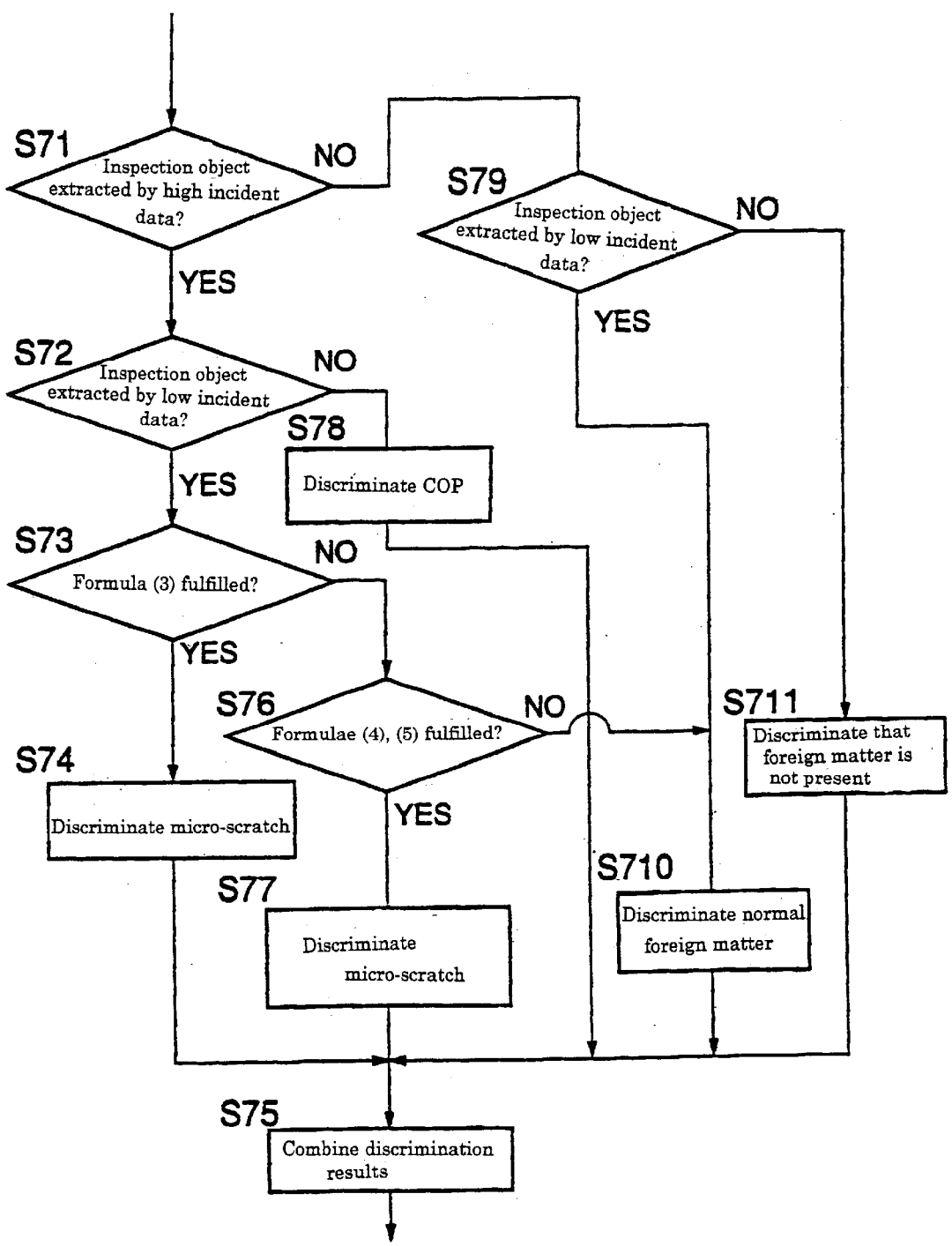
FIG. 11 is a view showing one example of a detailed flow chart of the measurement process of a wafer with a membrane after CMP process in the surface inspection apparatus according to a preferred embodiment of the present invention.

FIG. 11 shows one example of a detailed flow chart of the measuring process of a wafer with a membrane after CMP process.

The discrimination section 160 carries out the discrimination of the kind of the inspection object every coordinate in the surface of the inspected object on the basis of the extraction process of the inspection object data carried out in Step S4 of the flow chart of FIG. 9. The method for discriminating the kind of the inspection object is as shown in the flow chart of FIG. 11.

First, in Step S71, judgment is made if the inspection object is extracted in the high incident data. If the inspection object is extracted in the high incident data, the procedure proceeds to Step S72.

In Step S72, judgment is made if the inspection object is extracted in the low incident data. If the inspection object is extracted in the low incident data, the procedure proceeds to Step S73.

In Step S73, judgment is made if the following formula (3) is fulfilled. high incident scattered level low incident scattered level>1.5 . . . (3) Here, the scattered level is a numerical value indicative of the strength of the scattered light. The formula (3) is a formula to judge if the ratio between the strengths of the scattered light on the high incident side and the low incident side is above a predetermined level. The constant 1.5 is sometimes different depending on the CMP device.

If the formula (3) is fulfilled, the procedure proceeds to Step S74.

In Step S74, the kind of the inspection object is discriminated to be a micro-scratch, and the procedure proceeds to Step S75.

In Step S75, the discrimination result of the kind of the inspection object is combined with the discrimination result of the kind of the other inspection object on the surface of a bare wafer, and the procedure proceeds to Step S8 (FIG. 9), and the discrimination result of the kind of the inspection object is displayed on the display section 130.

In Step S73, if the formula (3) is not fulfilled, the procedure proceeds to Step S76.

In Step S76, judgment is made if the following formulae (4) and (5) are fulfilled.

high incident scattered level/low incident scattered level>1.0 . . . (4)

G (high incident scan area, high incident scattered light quantity)/G low incident scan area, low incident scattered light quantity)>2 . . . (5)

Here, the scattered level is a numerical value indicative of the strength of the scattered light. The formula (4) is a formula for judging if the ratio between the strengths of the scattered light on the high incident side and the low incident side is above a predetermined level. The constant 1.0 on the right side of the formula (4) is sometimes different depending on the CMP device.

Figure 13:
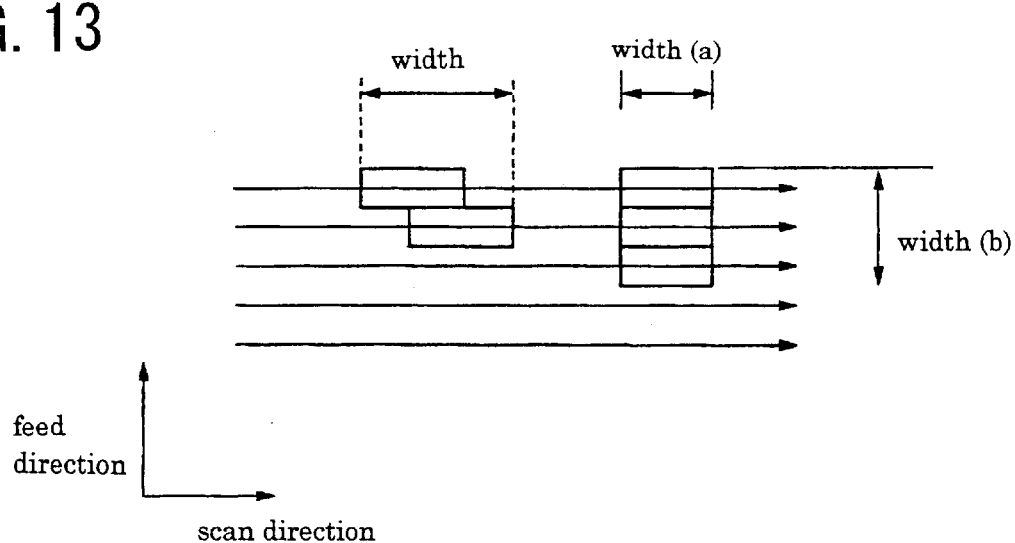
FIG. 13 is a schematic view showing the distribution of an inspection object in the surface inspection apparatus according to a preferred embodiment of the present invention.

G is a function with the scan area and the scattered light quantity as a variable. The scan area is a variable indicative of the scattered range of the scattered light. The scan area is obtained, for example, making use of the width of the inspection object, as shown in FIG. 13 (a schematic view showing the distribution of the inspection objects). The scattered light quantity is a variable indicative of the strength of the scattered light. The formula (5) is a formula for judging if the ratio between the functions due to the strength of the scattered light and the scattered range of the scattered light on the high incident side and the low incident side is above a predetermined value. The constant 2 on the right side of the formula (5) is sometimes different depending on the CMP device.

If the formulae (4) and (5) are fulfilled, the procedure proceeds to Step S77.

In Step S77, the kind of the inspection object is discriminated to be micro-scratch, and the procedure proceeds to Step S75. In Step S75, the discrimination results are combined as described previously.

In Step S76, if the formula (4) or (5) is not fulfilled, the procedure proceeds to Step S710. In Step S710, the kind of the inspection object is discriminated to be normal foreign matter, and the procedure proceeds to Step S75. In Step S75, the discrimination results are combined as described previously.

In Step S72, if the inspection object is not extracted in the low incident data, the procedure proceeds to Step S78. In Step S78, the kind of the inspection object is discriminated to be COP (crystal defect), and the procedure proceeds to Step S75. In Step S75, the discrimination results are combined as described previously.

In Step S71, if the inspection object is not extracted in the high incident data, the procedure proceeds to Step S79.

In Step S79, judgment is made if the inspection object is extracted in the low incident data. If the inspection object is extracted, the procedure proceeds to Step S710.

In Step S710, the inspection object is discriminated to be normal foreign matter, and the procedure proceeds to Step S75.

In Step S75, the discrimination results are combined as described previously.

In Step S79, if the inspection object is not extracted in the low incident data, the procedure proceeds to Step S711. In Step S711, judgment is made that the inspection object is not present (foreign matter or micro-scratch is not present), and the procedure proceeds to Step S75. In Step S75, the discrimination results are combined as described previously.

Table 2 shows a discrimination table of the kind of the inspection object of a wafer with a membrane after the CMP process by the flow chart of FIG. 11.

In Table 2, G is a function with the scan area and the scattered light quantity as a variable.

The inspection result, for example, as shown in FIG. 8, is obtained by the above-described measuring process.

In FIG. 8, the inspection objects A, E, F are detected as foreign matter (Particle). The inspection object B is detected as COP (crystal defect). The inspection object C is detected as a Micro-scratch. The inspection object D is detected as a Micro-scratch.

According to the present invention, the separation measurement between the COP (crystal defect) and foreign matter can be carried out correctly on the basis of the difference of the strength of the scattered light of the first luminous flux and the second luminous flux, and the scattered range of the first luminous flux and the second luminous flux.

According to the present invention, the inspection objects, which have been difficult to separate and measure, such as COP (crystal defect), micro-scratch, thin foreign matter produced mainly in the surface polishing process, can be separated and measured.

TABLE 1

| Inspection object | Inspection object extracted in high incident data? | Inspection object extracted in low incident data? | Formula (1) fulfilled? | Formula (2) fulfilled? |
| --- | --- | --- | --- | --- |
| Thin foreign matter | Extracted | Extracted | Fulfilled | Fulfilled |
| COP (crystal defect) | Extracted | Extracted | Fulfilled | Not fulfilled |
| | Extracted | Not extracted | | |
| Normal foreign matter | Extracted | Extracted | Not fulfilled | |
| | Not extracted | Extracted | | |
| No inspection object | Not extracted | Not extracted | | |

Formula (1)

high incident scattered level/low incident scattered level>1.5

Formula (2)

F (high incident scan time, high incident scattered light quantity)/F (low incident scan time, low incident scattered light quantity)>2

TABLE 2

| Inspection object | Inspection object extracted in high incident data? | Inspection object extracted in low incident data? | Formula (3) fulfilled? | Formulae (4), (5) fulfilled? |
| --- | --- | --- | --- | --- |
| Micro-scratch | Extracted | Extracted | Fulfilled | |
| | Extracted | Extracted | Not fulfilled | Fulfilled |
| COP (crystal defect) | Extracted | Not extracted | | |
| Normal foreign matter | Extracted | Extracted | Not fulfilled | Not fulfilled |
| | Not extracted | Extracted | | |
| No inspection object | Not extracted | Not extracted | | |

Formula (3)

high incident scattered level/low incident scattered level>1.5

Formula (4)

high incident scattered level/low incident scattered level>1.0

Formula (5)

G (high incident scan area, high incident scattered light quantity)/G (low incident scan area, low incident scattered light quantity)>2

What is claimed is:

1. A surface inspection apparatus comprising:
   a light source section for emitting a first luminous flux and a second luminous flux;

a first irradiation optical system in which the first luminous flux is irradiated on the surface of an inspected object at a first irradiation angle;

a second irradiation optical system in which the second luminous flux is irradiated on the surface of an inspected object at a second irradiation angle different from the first irradiation angle;

a light receiving optical system for receiving scattered light for the first luminous flux irradiated by the first irradiation optical system and produced from an inspection object on the surface of an inspected object and scattered light of the second luminous flux irradiated by the second irradiation optical system and produced from an inspection object on the surface of an inspected object;

a first light receiving section for converting the scattered light of the first luminous flux received by the light receiving optical system into a first light receiving signal;

a second light receiving section for converting the scattered light of the second luminous flux received by the light receiving optical system into a second light receiving signal;

a displacement section for relatively displacing an inspected object and an irradiation luminous flux of the irradiation optical system; and a discrimination section for discriminating the kind of an inspection object on an inspected object on the basis of the strength of the scattered light of the first and second light receiving signals, and the scattered range of the scattered light of the first and second light receiving signals, wherein the discrimination section carries out the scattered light quantity ratio process for obtaining the strength ratio of the scattered light of the first and second light receiving signals, and the scattered range detection process for obtaining the scattered range of the scattered light according to whether or not the first and second light receiving signals is above a predetermined level.

2. A surface inspection apparatus according to claim 1, wherein the first characteristic of the first luminous flux emitted by the light source section and the second characteristic of the second luminous flux emitted by the light source section lie in wavelength of luminous flux or polarized-light component.

3. A surface inspection apparatus according to claim 1, wherein a first irradiation angle of the first irradiation optical system is set to be smaller than a second irradiation angle of the second irradiation optical system.

4. A surface inspection apparatus according to claim 1, wherein the discrimination section carries out the discrimination processes as described below every position of the surface of an inspected object:

(A) when judgment is made that the scattered light generated from the inspection object is present in only one of either the first light receiving signal or the second light receiving signal, the first discrimination process for discriminating that the kind of the inspection object is a first inspection object is carried out;

(B) when judgment is made that the scattered light generated from the inspection object is present in both the first light receiving signal and the second light receiving signal, the ratio between the strength of scattered light of the first light receiving signal and the strength of scattered light of the second light receiving signal is obtained, and if the ratio is at a level above a predetermined level, the second discrimination process for discriminating that the kind of the inspection object is a second inspection object is carried out;

(C) when judgment is made that the scattered light generated from the inspection object is present in both the first light receiving signal and the second light receiving signal, the ratio between the strength of scattered light of the first light receiving signal and the strength of scattered light of the second light receiving signal is obtained, and the ratio is at a level above a predetermined level, and further, a first function due to the strength of scattered light and the scattered range of scattered light of the first light receiving signal and a second function due to the strength of scattered light and the scattered range of scattered light of the second light receiving signal are obtained, and when the ratio therebetween is at a value above a predetermined value, the third discrimination process for discriminating that the kind of the inspection object is a third inspection object is carried out; and (D) when judgment is made that scattered light generated from the inspection object not falling under the process is present in the first light receiving signal or the second light receiving signal, the discrimination process for discriminating that the kind of the inspection object is normal foreign matter is carried out.

5. A surface inspection apparatus according to claim 1, wherein the kind of the inspection object discriminated by the discrimination section is decided according to what kind the inspected object is.

6. A surface inspection apparatus comprising:

a tight source section for emitting a first luminous flux and a second luminous flux;

a first irradiation optical system in which the first luminous flux is irradiated on the surface of an inspected object at a first irradiation angle;

a second irradiation optical system in which the second luminous flux is irradiated on the surface of an inspected object at a second irradiation angle different from the first irradiation angle;

a light receiving optical system for receiving scattered light of the first luminous flux irradiated by the first irradiation optical system and produced from an inspection object on the surface of an inspected object and scattered light of the second luminous flux irradiated by the second irradiation optical system and produced from an inspection object on the surface of an inspected object;

a first light receiving section for converting the scattered light of the first luminous flux received by the light receiving optical system into a first light receiving signal;

a second light receiving section for converting the scattered light of the second luminous flux received by the light receiving optical system into a second light receiving signal;

a displacement section for relatively displacing an inspected object and an irradiation luminous flux of the irradiation optical system; and a discrimination section for discriminating the kind of an inspection object on an inspected object on the basis of the strength of the scattered light of the first and second light receiving signals, and the scattered range of the scattered light of the first and second light receiving signals, wherein the kind of the inspection object discriminated by the discrimination section is decided according to what kind the inspected object is, and wherein where an inspected object is a bare wafer, the discrimination section discriminates COP (crystal defect) as a first inspection object by a first discrimination process, discriminates COP (crystal defect) as a second inspection object by a second discrimination process, and discriminates a thin foreign matter as a third inspection object by a third discrimination process.

7. A surface inspection apparatus comprising:

a light source section for emitting a first luminous flux and a second luminous flux;

a first irradiation optical system in which the first luminous flux is irradiated on the surface of an inspected object at a first irradiation angle;

a second irradiation optical system in which the second luminous flux is irradiated on the surface of an inspected object at a second irradiation angle different from the first irradiation angle;

a light receiving optical system for receiving scattered light of the first luminous flux irradiated by the first irradiation optical system and produced from an inspection object on the surface of an inspected object and scattered light of the second luminous flux irradiated by the second irradiation optical system and produced from an inspection object on the surface of an inspected object;

a first light receiving section for converting the scattered light of the first luminous flux received by the light receiving optical system into a first light receiving signal;

a second light receiving section for converting the scattered light of the second luminous flux received by the light receiving optical system into a second light receiving signal;

a displacement section for relatively displacing an inspected object and an irradiation luminous flux of the irradiation optical system; and a discrimination section for discriminating the kind of an inspection object on an inspected object on the basis of the strength of the scattered light of the first and second light receiving signals, and the scattered range of the scattered light of the first and second light receiving signals, wherein the kind of the inspection object discriminated by the discrimination section is decided according to what kind the inspected object is, and wherein where an inspected object is a semiconductor wafer after CMP (chemical mechanical process) process of a wafer with a membrane, the discrimination section discriminates COP (crystal defect) as a first foreign matter by a first discrimination process, discriminates a micro-scratch as a second foreign matter by a second discrimination process, and discriminates a micro-scratch as a third foreign matter by a third discrimination process.

8. A surface inspection method, in a method for discriminating a foreign matter in a state for relatively displacing an inspected object and an irradiation luminous flux of an irradiation optical system by a displacement section, comprising:

a step of irradiating a first luminous flux on the surface of an inspected object at a first irradiation angle, and irradiating a second luminous flux on the surface of an inspected object at a second irradiation angle different from the first irradiation angle;

a step of receiving scattered light of the first luminous flux and the second luminous flux irradiated by the irradiation optical system and produced from an inspection object on the surface of an inspected object by the first light receiving section and the second light receiving section;

a step of converting the scattered light of the first luminous flux received by the first light receiving section into a first light receiving signal, and converting the scattered light of the second luminous flux received by the second light receiving section into a second light receiving signal; and a step of discriminating the kind of an inspection object on an inspected object on the basis of the strength of the scattered light of the first and second light receiving signals, and the scattered range of the scattered light of the first and second light receiving signals.

9. A surface inspection method comprising:

a step of emitting a first luminous flux and a second luminous flux;

a step of irradiating the first luminous flux on the surface of an inspected object at a first irradiation angle;

a step of irradiating the second luminous flux on the surface of an inspected object at a second irradiation angle different from the first irradiation angle;

a step of receiving scattered light of the first luminous flux produced from an inspection object on the surface of an inspected object and scattered light of the second luminous flux produced from an inspection object on the surface of an inspected object;

a step of converting the scattered light of the first luminous flux into a first light receiving signal;

a step of converting the scattered light of the second luminous flux into a second light receiving signal;

a step of relatively displacing an inspected object and an irradiation luminous flux; and a step of discriminating the kind of an inspection object on an inspected object on the basis of the strength of the scattered light of the first and second light receiving signals, and the scattered range of the scattered light of the first and second light receiving signals.

10. A surface inspection method according to claim 9, wherein the first characteristic of the first luminous flux and the second characteristic of the second luminous flux lie in wavelength of luminous flux or polarized-light component.

11. A surface inspection method according to claim 9, wherein a first irradiation angle is set to be smaller than a second irradiation angle.

12. A surface inspection method according to claim 9, wherein in the discrimination step, there carries out carries out the scattered light quantity ratio process for obtaining the strength ratio of the scattered light of the first and second light receiving signals, and the scattered range detection process for obtaining the scattered range of the scattered light according to whether or not the first and second light receiving signals is above a predetermined level.

13. A surface inspection method according to claim 9, wherein in the discrimination step, there carries out the discrimination processes as described below every position of the surface of an inspected object:

(A) when judgment is made that the scattered light generated from the inspection object is present in only one of either the first light receiving signal or the second light receiving signal, the first discrimination process for discriminating that the kind of the inspection object is a first inspection object is carried out;

(B) when judgment is made that the scattered light generated from the inspection object is present in both the first light receiving signal and the second light receiving signal, the ratio between the strength of scattered light of the first light receiving signal and the strength of scattered light of the second light receiving signal is obtained, and if the ratio is at a level above a predetermined level, the second discrimination process for discriminating that the kind of the inspection object is a second inspection object is carried out;

(C) when judgment is made that the scattered light generated from the inspection object is present in both the first light receiving signal and the second light receiving signal, the ratio between the strength of scattered light of the first light receiving signal and the strength of scattered light of the second light receiving signal is obtained, and the ratio is at a level above a predetermined level, and further, a first function due to the strength of scattered light and the scattered range of scattered light of the first light receiving signal and a second function due to the strength of scattered light and the scattered range of scattered light of the second light receiving signal are obtained, and when the ratio therebetween is at a value above a predetermined value, the third discrimination process for discriminating that the kind of the inspection object is a third inspection object is carried out; and (D) when judgment is made that scattered light generated from the inspection object not falling under the process is present in the first light receiving signal or the second light receiving signal, the discrimination process for discriminating that the kind of the inspection object is normal foreign matter is carried out.

14. A surface inspection method according to claim 9, wherein in the discrimination step, the kind of the inspection object to be discriminated is decided according to what kind the inspected object is.

15. A surface inspection method according to claim 14, wherein where an inspected object is a bare wafer, a first discrimination process discriminates COP (crystal defect) as a first inspection object, a second discrimination process discriminates COP (crystal defect) as a second inspection object, and a third discrimination process discriminates a thin foreign matter as a third inspection object.

16. A surface inspection method according to claim 14, wherein where an inspected object is a semiconductor wafer after CMP (chemical mechanical process) process of a wafer with a membrane, a first discrimination process discriminates COP (crystal defect) as a first foreign matter, a second discrimination process discriminates a micro-scratch as a second foreign matter, and a third discrimination process discriminates a micro-scratch as a third foreign matter.

17. A surface inspection apparatus comprising:
a means for emitting a first luminous flux and a second luminous flux;
a means for irradiating the first luminous flux on the surface of an inspected object at a first irradiation angle;
a means for irradiating the second luminous flux on the surface of an inspected object at a second irradiation angle different from the first irradiation angle;
a means for receiving scattered light of the first luminous produced from an inspection object on the surface of an inspected object and scattered light of the second luminous flux produced from an inspection object on the surface of an inspected object;
a means for converting the scattered light of the first luminous flux received by the light receiving means into a first light receiving signal;
a means for converting the scattered light of the second luminous flux into received by the light receiving means a second light receiving signal;
a means for relatively displacing an inspected object and an irradiation luminous flux; and
a means for discriminating the kind of an inspection object on an inspected object on the basis of the strength of the scattered light of the first and second light receiving signals, and the scattered range of the scattered light of the first and second light receiving signals.

18. A surface inspection apparatus according to claim 17, wherein the first characteristic of the first luminous flux emitted by the light emitting means and the second characteristic of the second luminous flux emitted by the light emitting means lie in wavelength of luminous flux or polarized-light component.

19. A surface inspection apparatus according to claim 18, wherein a first irradiation angle is set to be smaller than a second irradiation angle.

20. A surface inspection apparatus according to claim 17, wherein in the discrimination means, there carries out the scattered light quantity ratio process for obtaining the strength ratio of the scattered light of the first and second light receiving signals, and the scattered range detection process for obtaining the scattered range of the scattered light according to whether or not the first and second light receiving signals is above a predetermined level.

21. A surface inspection apparatus according to claim 17, wherein in the discrimination means, there carries out the discrimination processes as described below every position of the surface of an inspected object:

(A) when judgment is made that the scattered light generated from the inspection object is present in only one of either the first light receiving signal or the second light receiving signal, the first discrimination process for discriminating that the kind of the inspection object is a first inspection object is carried out;

(B) when judgment is made that the scattered light generated from the inspection object is present in both the first light receiving signal and the second light receiving signal, the ratio between the strength of scattered light of the first light receiving signal and the strength of scattered light of the second light receiving signal is obtained, and if the ratio is at a level above a predetermined level, the first discrimination process for discriminating that the kind of the inspection object is a second inspection object is carried out;

(C) when judgment is made that the scattered light generated from the inspection object is present in both the first light receiving signal and the second light receiving signal, the ratio between the strength of scattered light of the first light receiving signal and the strength of scattered light of the second light receiving signal is obtained, and the ratio is at a level above a predetermined level, and further, a first function due to the strength of scattered light and the scattered range of scattered light of the first light receiving signal and a second function due to the strength of scattered light and the scattered range of scattered light of the second light receiving signal are obtained, and when the ratio therebetween is at a value above a predetermined value, the third discrimination process for discriminating that the kind of the inspection object is a third inspection object is carried out; and (D) when judgment is made that scattered light generated from the inspection object not falling under the process is present in the first light receiving signal or the second light receiving signal, the discrimination process for discriminating that the kind of the inspection object is normal foreign matter is carried out.

22. A surface inspection apparatus according to claim 17, wherein the kind of the inspection object discriminated by the discrimination means is decided according to what kind the inspected object is.

23. A surface inspection apparatus according to claim 22, wherein where an inspected object is a bare wafer, the discrimination means discriminates COP (crystal defect) as a first inspection object by a first discrimination process, discriminates COP (crystal defect) as a second inspection object by a second discrimination process, and discriminates a thin foreign matter as a third inspection object by a third discrimination process.

24. A surface inspection apparatus according to claim 22, wherein where an inspected object is a semiconductor wafer after CMP (chemical mechanical process) process of a wafer with a membrane, the discrimination means discriminates COP (crystal defect) as a first foreign matter by a first discrimination process, discriminates a micro-scratch as a second foreign matter by a second discrimination process, and discriminates a micro-scratch as a third foreign matter by a third discrimination process.

* * * * *